(12) United States Patent
Graupe et al.

(10) Patent No.: US 8,391,986 B2
(45) Date of Patent: Mar. 5, 2013

(54) APPARATUS FOR MANAGING A NEUROLOGICAL DISORDER

(75) Inventors: Daniel Graupe, Highland Park, IL (US);
Daniela Tuninetti, Chicago, IL (US);
Ishita Basu, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/992,265

(22) PCT Filed: May 12, 2009

(86) PCT No.: PCT/US2009/043637
§ 371 (c)(1),
(2), (4) Date: Nov. 11, 2010

(87) PCT Pub. No.: WO2009/140283
PCT Pub. Date: Nov. 19, 2009

(65) Prior Publication Data
US 2011/0098780 A1    Apr. 28, 2011

Related U.S. Application Data

(60) Provisional application No. 61/052,870, filed on May 13, 2008.

(51) Int. Cl.
*A61N 1/00* (2006.01)
(52) U.S. Cl. .......................................................... 607/45
(58) Field of Classification Search ................ 600/45; 607/1, 2, 45, 46
See application file for complete search history.

(56) References Cited

U.S. PATENT DOCUMENTS

| 6,016,449 | A |   | 1/2000 | Fischell |
| 6,094,598 | A | * | 7/2000 | Elsberry et al. ................ 607/116 |
| 6,227,203 | B1 | * | 5/2001 | Rise et al. ...................... 128/898 |
| 6,463,328 | B1 |   | 10/2002 | John |
| 7,006,872 | B2 |   | 2/2006 | Gielen |
| 7,463,927 | B1 | * | 12/2008 | Chaouat .......................... 607/46 |
| 2002/0116042 | A1 |   | 8/2002 | Boling |
| 2002/0161403 | A1 | * | 10/2002 | Meadows et al. ................. 607/1 |

(Continued)

FOREIGN PATENT DOCUMENTS

| WO | 2004034880 | 4/2004 |
| WO | 2006110206 | 10/2006 |

(Continued)

OTHER PUBLICATIONS

Daniel Graupe, et al., "Adaptively controlling deep brain stimulation in essential tremor patient via surface electromyography", Neurological Research 2010 vol. 32 No. 9 899.

(Continued)

*Primary Examiner* — George Manuel
*Assistant Examiner* — Robert N Wieland
(74) *Attorney, Agent, or Firm* — Michael Best & Friedrich LLP (57) ABSTRACT

A system that incorporates teachings of the present disclosure may include, for example, a Neuro Sensing and Stimulation Device having a conductive lead for implanting in a brain of a living entity, a sensor coupled to the conductive lead for collecting data associated with one or more electrical signals detected in the conductive lead, a stimulator coupled to the conductive lead to apply one or more electrical signals thereto, and a controller. The controller can be operable to collect data associated with one or more electrical signals detected in the conductive lead, determine a stimulation sequence from the collected data, and direct the stimulator to apply on the conductive lead one or more electrical signals determined from the stimulation sequence. Additional embodiments are disclosed.

35 Claims, 5 Drawing Sheets

U.S. PATENT DOCUMENTS

| | | | |
|---|---|---|---|
| 2003/0195602 A1 | 10/2003 | Boling | |
| 2005/0187589 A1 | 8/2005 | Wallace | |
| 2005/0240086 A1 | 10/2005 | Akay | |
| 2006/0058854 A1* | 3/2006 | Abrams et al. | 607/45 |
| 2006/0217781 A1 | 9/2006 | John | |
| 2007/0025608 A1* | 2/2007 | Armstrong | 382/132 |
| 2007/0208212 A1 | 9/2007 | DiLorenzo | |
| 2007/0239054 A1* | 10/2007 | Giftakis et al. | 600/513 |
| 2008/0033508 A1 | 2/2008 | Frei | |
| 2008/0046012 A1* | 2/2008 | Covalin et al. | 607/2 |
| 2008/0058773 A1 | 3/2008 | John | |
| 2009/0082691 A1* | 3/2009 | Denison et al. | 600/544 |
| 2010/0094377 A1 | 4/2010 | Graupe | |
| 2010/0217341 A1 | 8/2010 | John | |
| 2011/0251583 A1* | 10/2011 | Miyazawa et al. | 604/503 |

FOREIGN PATENT DOCUMENTS

| | | |
|---|---|---|
| WO | 2007058788 | 5/2007 |
| WO | 2008027233 | 3/2008 |

OTHER PUBLICATIONS

Patent Cooperation Treaty, "Written Opinion of the International Searching Authority", ISA/EP, by Officer David Pereda Cubian, in PCT Application No. PCT/US2009/043637, document of 8 pages dated Nov. 17, 2010.

Patent Cooperation Treaty, "International Search Report and Written Opinion", ISA/EP, by Officer David Pereda Cubian in PCT Application No. PCT/US09/043637; Document of 3 pages dated Jun. 8, 2009.

Graupe, "Principles of Artificial Neural Networks", University of Illinois, Chicago, USA; World Scientific, Advanced Series on Circuits and Systems—vol. 6 2nd Edition (Cover).

Graupe, "Time Series Analysis, Identification and Adaptive Filtering", Robert Krieger Publishing Company, Malabar, Florida; 2nd Edition (Cover).

* cited by examiner

APPARATUS FOR MANAGING A NEUROLOGICAL DISORDER

FIELD OF THE DISCLOSURE

The present disclosure relates generally to neurological disorders, and more specifically to an apparatus for managing a neurological disorder.

BACKGROUND

Neurological disorders such as Parkinson's disease can be a chronic, progressive neurodegenerative movement disorder whose primary symptoms include tremors, rigidity, slow movement, poor balance and difficulty walking. When a person has Parkinson's disease, his/her dopamine-producing cells in the brain begin to die. Dopamines are responsible for sending information to the parts of the brain that control movement and coordination. Hence, as the amount of dopamine produced decreases, messages from the brain directing the body how and when to move are delivered in a slower fashion, leaving a person incapable of initiating and controlling movements in a normal way.

Deep Brain Stimulation (DBS) is a surgical therapy for movement disorders that represents an advancement in the treatment of Parkinson over the last 50 years. DBS uses a surgically implanted, battery-operated thin neuron-stimulator to reverse in large part the abnormal function of the brain tissue in the region of the stimulating electrode.

Commercially available DBS systems typically include a neuron-stimulator, an extension, and a lead. The neuron-stimulator is placed under skin operating as a battery powered electrical impulse generator implanted in the abdomen. The extension is a wire also placed under the skin (from the head, down the neck, to the abdomen) to bring the signals generated by neuron-stimulator to the lead. The lead is an insulated coiled wire with four electrodes implanted deeply in the brain to release the electrical impulse.

DETAILED DESCRIPTION

An embodiment of the present disclosure entails a Neuro Sensing and Stimulation Device (NSSD) having a conductive lead for implanting in a brain of a living entity, a sensor coupled to the conductive lead for collecting data associated with one or more electrical signals detected in the conductive lead, a stimulator coupled to the conductive lead to apply one or more electrical signals thereto, and a controller. The controller can be operable to collect data associated with one or more electrical signals detected in the conductive lead, determine a stimulation sequence from the collected data, and direct the stimulator to apply on the conductive lead one or more electrical signals determined from the stimulation sequence.

An embodiment of the present disclosure entails a Controlling Device (CD) having a controller operable to direct a Neuro Sensing and Stimulation Device (NSSD) having a conductive lead implanted in a brain of a living entity to supply sensing data derived from electrical activity sensed from the brain and for stimulating the brain, receive from the NSSD sensing data collected by the NSSD by way of the conductive lead, determine stimulation instructions from the collected sensing data, and direct the NSSD to apply one or more electrical signals to the brain of the living entity according to the stimulation instructions.

An embodiment of the present disclosure entails a Closed Loop Neural Device (CLND) having a conductive lead for implanting in a portion of a brain of a living entity, a stimulation generator coupled to the conductive lead for applying signals to the portion of the brain, a neural sensor coupled to the conductive lead for sensing electrical activity in the portion of the brain, a controller coupled to the stimulation generator and the sensor to control the signals applied by the stimulation generator according to the electrical activity sensed in the portion of the brain, and a power supply to supply energy to the stimulation generator, the sensor and the controller.

The signals applied by the stimulation generator of the CLND on the conductive lead can correspond to a sequence of stimulation signals. The controller of the CLND can control by way of the stimulation generator one or more characteristics of the stimulation signals. The one or more characteristics can include without limitation at least one of an amplitude, an inter-pulse interval, and a pulse width of the stimulation signals. The controller of the CLND can communicate with at least one of the stimulation generator and the sensor by wireless or wireline means. The neural sensor can be an integral part of the controller. At least a portion the CLND can be implanted in the living entity. The power supply can be charged according to wireless radio waves or body heat converted by the power pack into stored energy. The power pack can also be inductively coupled to a power source that generates the radio waves.

The CLND can also have a tremor sensor coupled to the controller and the living entity. The controller can be operable to detect tremors in the living entity by way of the tremor sensor, and direct the stimulation generator to apply one or more signals to the conductive leads to mitigate the detected tremors. The controller can be operable to distinguish between tremors and common motion of the living entity. In an embodiment, the tremor sensor can correspond to an accelerometer to detect tremors. The tremor sensor can be implanted in the living entity or coupled to an external surface of the living entity such as an appendage of the living entity. The controller can be operable to determine when to direct the stimulation generator to apply signals to the brain of the living entity according to at least one of signals supplied by the tremor sensor and signals supplied by the neural sensor coupled to the conductive lead.

The controller CLND can also be operable to monitor electrical activity in the brain by way of the neural sensor while the stimulation generator is prevented by the controller from supplying signals to the conductive lead. The signals applied to the conductive lead by the stimulation generator can be periodic signals having a duty cycle controlled by the controller. The CLND can also have a plurality of controllable switches coupled to the stimulation generator and the neural sensor respectively at one end, and the conductive lead at another end for controllably isolating and conductively coupling the stimulation generator and the sensor to the conductive lead. The plurality of controllable switches can be controlled by one of the controller, the stimulation generator, and the neural sensor. The plurality of controllable switches can be optical-isolation switches. An impedance of each of the plurality of controllable switches can be adjustable. The controller of the CLND can be operable to control at least one of the plurality of switches to match a collective impedance of said switch and the conductive lead with a corresponding impedance of the portion of the brain coupled to the conductive lead.

The CLND can also have a wireless transceiver. The controller can be operable to detect a low energy state in the power pack, and transmit a wireless signal to a receiving device that emits an alert to indicate the low energy state. Based on any combination of embodiments of the CLND, the CLND can be operable to mitigate at least one of a plurality of diseases including without limitation Parkinson's disease, a neurological tremor disease, Alzheimer's disease, and Epilepsy.

Figure 1:
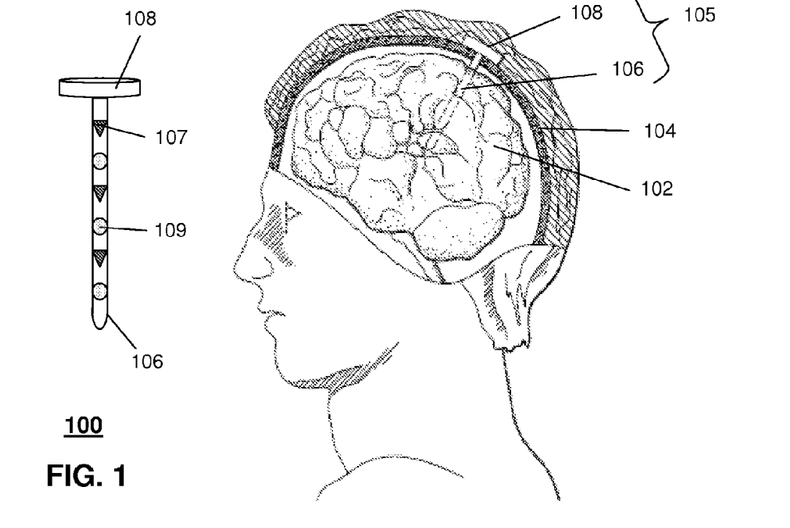
FIG. 1 depicts an illustrative embodiment of a patient with an implanted portion of a Neuro Sensing and Stimulation Device (NSSD)

FIG. 1 depicts an illustrative embodiment of a patient 100 with an implanted portion of a Neuro Sensing and Stimulation Device (NSSD) 105. The NSSD 105 can include a conductive lead 106 implanted in the brain 102 of the patient 100. The conductive lead 106 can be constructed from any common biocompatible conductive materials. The conductive lead 106 can be implanted in a section of the brain 102 that minimizes damage to the patient 100 (cognitively or otherwise) and provides a means to mitigate neurological diseases. The conductive lead 106 can be implanted by a brain surgeon by drilling a hole through the skull 104 of the patient 100 and carefully placing the conductive lead 106 in a desirable location of the brain 102. The conductive lead 106 can be a stiff or flexible conductive lead to provide the specialist flexibility in the implantation process. The conductive lead 106 can be a section of a longer probe of several conductive leads with each section insulated from the other.

The conductive lead 106 can be connected to a base unit 108 which can be adapted to sense electrical signals in the brain 102 (and thereby a level of dopamine), and electrically stimulate the brain 102 to mitigate a neurological condition. For illustration purposes, the base unit 108 and conductive lead 106 are shown to the left of the patient 100 in FIG. 1 before implantation. The conductive lead 106 can have electrodes for stimulation 107 and electrodes for sensing 109 brain activity. Electrodes 107 and 109 can be electrically insulated from each other. By isolating the stimulation and sensing electrodes 107, 109, the base unit 108 can be adapted to sense and stimulate the patient's brain in sequence or simultaneously.

The base unit 108 as illustrated in FIG. 1 can be small enough to be camouflaged in whole or in part by the patient's hair. Alternatively, the base unit 108 can be implanted below a skin of the patient's head. The form factor of the base unit 108 can also be contoured to closely match the curved skull surface of the patient 100.

Figure 2:
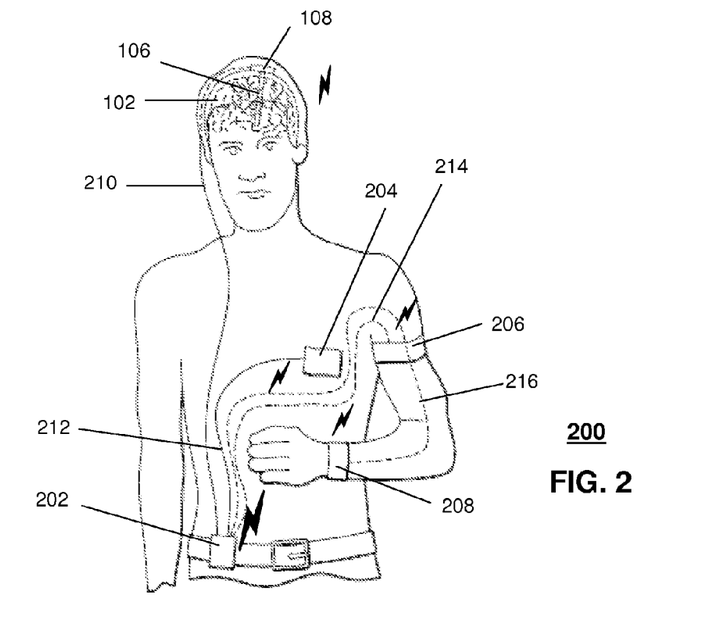
FIG. 2 depicts an illustrative embodiment of the NSSD operationally coupled to a controlling device and a tremor sensor.

FIG. 2 depicts an illustrative embodiment of the NSSD 105 communicatively coupled to a controlling device 202 which in turn is communicatively coupled to a plurality of tremor sensors 204, 208, or 210. The controlling device 202 can be communicatively coupled to the NSSD 105 by wire 210 or wirelessly. The controller device 202 can also be communicatively coupled to the tremor sensors 204, 206, 208 by wire (212, 214, or 216) or wirelessly. In one embodiment the tremor sensor 204 can have a form factor of a patch placed on the chest of the patient 100. In another embodiment, the tremor sensor 206 can have a form factor of an armband placed around the biceps of the patient 100. In yet another embodiment, the tremor sensor 208 can have a form factor of a wristband placed around the wrist of the patient 100. Tremor sensors can also be placed on other parts of the patient's body such as for example a thigh, calf, and so on.

The tremor sensors 204, 206 or 208 can utilize common electromyographic (EMG) technology with one or more EMG electrodes. The EMG electrodes of the tremor sensors 204 can be placed non-invasively on a surface of the patient as illustratively shown in FIG. 2, or can be partially implanted below a skin surface of the patient 100. The tremor sensors 204, 206, 208 can utilize any common technology for sensing a constriction of muscle or vibration of body limbs. The tremor sensors 204-208 can be used with a patient 100 to detect tremors in more than one section of the patient's body.

The controlling device 202 can receive sensing data from the NSSD 105 of FIG. 1 and the tremor sensors 204-208. The sensing data from the NSSD 105 can represent electrical signals sensed in the brain 102 by way of the sensor leads 109 of the conductive lead 106. The sensing data from the NSSD 105 can also indicate a lack or absence of electrical signals expected under normal circumstances. The sensing data from the NSSD 105 can be conveyed as digital information transmitted to the controlling device 202 as binary data or other suitable coding schemes which can be understood and processed by the controlling device 202.

The sensing data from the tremor sensors 204-208 can represent motion data which can be processed and thereby distinguished by the controlling device 202 as either normal or expected motion versus abnormal movements by the patient 100 (such as muscle cramps, muscle shakes, and so on). As will be explained shortly, the controlling device 202 can process the sensing data of the NSSD 105 of FIG. 1 and/or the tremor sensors 204-208 to determine whether a neurological abnormality has occurred or is about to occur. When a neurological abnormality has been detected or predicted by the controlling device 202, the controlling device 202 can in turn determine a stimulus strategy from the sensing data of the NSSD 105 and/or tremor sensors 204-208 which it can convey to the NSSD 105 to apply by way of stimulator leads 107 of the conductive lead 106 to mitigate the detected neurological abnormality.

Figure 3:
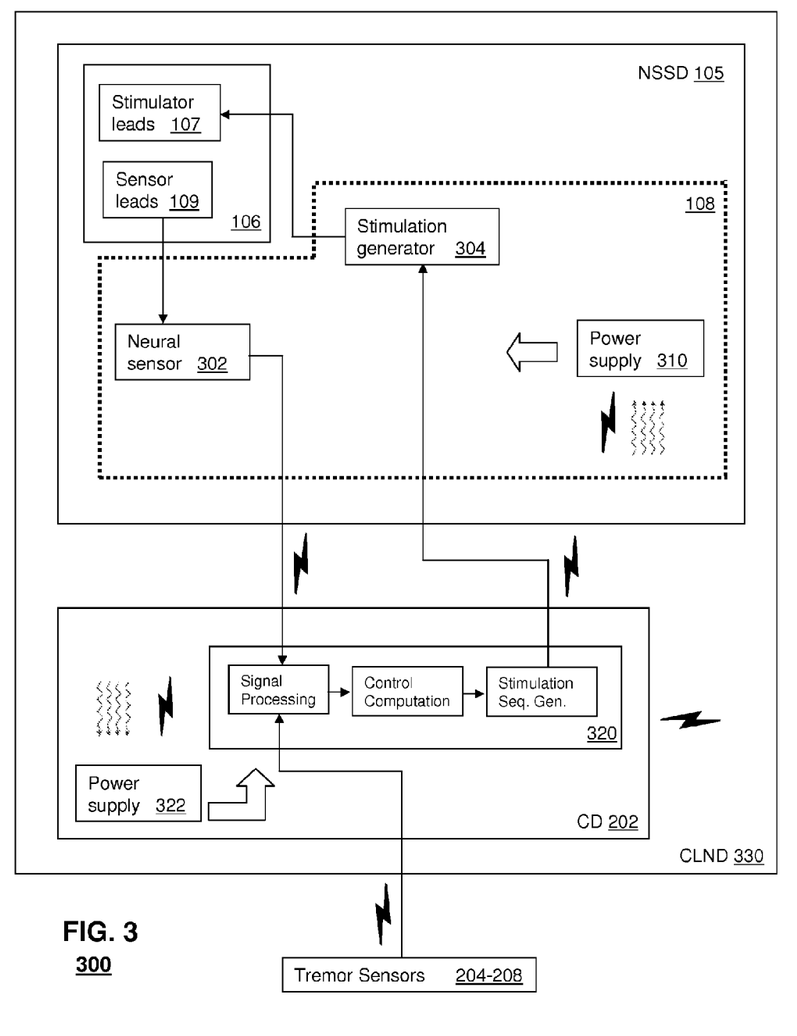
FIG. 3 depicts an illustrative embodiment of a functional block diagram of the NSSD, the controlling device, and the tremor sensor.

FIG. 3 depicts an illustrative embodiment of a functional block diagram 300 of the NSSD 105, the controlling device 202, and the tremor sensors 204-208. The NSSD 105 can comprise the conductive lead 106 (with stimulator leads 107 and sensor leads 109) coupled to the base unit 108. The base unit 108 can include a neural sensor 302, a stimulation generator 304, and a battery-operated power supply 310, each managed by a controller 320 in the controlling device 202. The neural sensor 302 can utilize common electrical sensing technology (such as an analog to digital converter or ADC) for sensing electrical signals in the brain 102 by way of the sensor leads 109. The neural sensor 302 can include or one or more common signal amplifiers and/or filters to improve the measurability and interpretation of the patient's brain activity.

The stimulation generator 304 can utilize common electrical generation technology (such as a digital to analog converter or DAC) to stimulate the brain 102 by way of the stimulator leads 107. The stimulation generator 304 can also utilize one or more common signal amplifiers and/or filters to produce desirable waveforms at desirable amplitudes. In cases where there may be a need to apply electrical signals at greater amplitudes than can be supplied by the battery-operated power supply 310, the stimulation generator 304 can also utilize common charge pump technology to increase the amplitude of signals generated by the DAC. The stimulation generator 304 can also include a random signal generator to create a stochastic signal sequence that can be applied to the brain 102. In some applications, it may be desirable to electrically isolate the neural sensor 302 from the stimulation generator 304 with common isolation devices such as transistors or other common switches.

The neural sensor 302 and the stimulation generator 304 can be coupled to the controller 320 by a wired interface or wireless interface. Wired access technologies utilized by either of the neural sensor 302 and the stimulation generator 304 to communicate with the controller 320 can include USB, Firewire, Ethernet, other common wired technologies, or a proprietary wired access technology suitable for the applications described herein. Wireless access technologies utilized by either of the neural sensor 302 and the stimulation generator 304 to communicate with the controller 320 can include Bluetooth, Wireless Fidelity (WiFi), Zigbee, other commonly known wireless access technologies, or a proprietary wireless technology especially suited for the applications described herein.

The controller 320 can utilize common computing technology such as a microprocessor, a digital signal processor (DSP), a microcontroller, a state machine, an application specific integrated circuit (ASIC), or other common computing technologies. The controller 320 can be equipped with common volatile and non-volatile memory to execute software instructions and perform data processing. The controller 320 can be programmed to enable the neural sensor 302 to measure electrical signals by way of the sensor leads 109. The controller 320 can process the sensing data provided by the neural sensor 302 to make determinations of the state of the patient 100. Based on these determinations, the controller 320 can direct the stimulation generator 304 to apply at the stimulator leads 107 a sequence of electrical stimulation signals.

The components of the base unit 108 described above can be powered by the battery-operated power supply 310 utilizing for example common power management technology. In one embodiment, the power supply 310 can include rechargeable batteries that can be recharged by a common trickle charger. The trickle charger can receive electrical energy from an external source (such as the controlling device 202) that connects to the trickle charger by way of a tethered wire supplying a DC signal thereto, or by inductive coupling to an electromagnetic charger. To bypass the need for tethering the power supply 310 to an external source, the trickle charger can be equipped with common technology that can derive electrical energy from a number of untethered sources.

For instance, the trickle charger can utilize common technology that generates an electrical charge from kinetic energy caused by the patient's movements. The trickle charger can also utilize common technology to generate an electrical charge from radio signals over a wide frequency spectrum. In yet another embodiment, the trickle charger can utilize common technology that generates electrical energy from a heat source such as the patient's body and/or ambient air. In another embodiment, the trickle charger can utilize common technology such as a solar cell to generate electrical energy from light. The trickle charger can utilize any of these technologies singly or in combination.

The NSSD 105 as described above can be coupled wirelessly or by tethered wire to the controlling device 202. With the computing resources of the controller 320 allows it utilize resource intensive signal processing algorithms to process the sensing data supplied by the NSSD 105 and/or the tremor sensors 204-208. Functionally, the controller 320 can perform signal processing, control computation, and stimulation sequence generation. The signal processing and control computation portions of the controller 320 can be programmed to utilize a common wavelet transform and/or a neural network to detect from the sensing data of the neural sensor 302 and/or the tremor sensors 204-208 a neural malfunction in the brain of the patient 100. Teachings of a wavelet transform and neural network can be found in D Graupe, Principles of Artificial Neural Networks, $2^{nd}$ edition, World Science Publishers, Singapore and Hackensack, N.J., 2007. Teachings from this reference are incorporated by reference in the present disclosure.

Alternatively or in combination, signal processing and control computation portions of the controller 320 can be programmed to utilize a common least squares identification algorithm to detect from the sampling data a neural malfunction in the brain of the patient 100. Teachings of a least squares identification can be found in D Graupe, Time Series Analysis, Identification and Adaptive Filtering, $2^{nd}$ edition, Krieger Publishing Co., Malabar, Fla., 1989. Teachings from this reference are incorporated by reference in the present disclosure.

Other signal processing algorithms that can be used by the controller 320 to detect or predict a neural malfunction from sensing data derived from the patient's brain and/or tremor sensors are contemplated by the present disclosure.

Once a malfunction is detected, the stimulation sequence generation portion of the controller 320 can determine a stimulation sequence which can be conveyed to the stimulation generator 324 by a wired or wireless interface.

The controller 320 can be powered by power supply 322. The power supply 322 can be battery-operated or powered by an external source. In the case of a battery-operated embodiment, the power supply 322 can utilize a trickle charger that utilizes any of the technologies described above for generating electrical energy from common sources such as heat, radio signals, light, kinetic energy, etc.

The controlling device 202 can also be communicatively coupled to the tremor sensors (204-208) by a wired or wireless interface. The power supply 322 of the controlling device 202 can power the tremor sensors 204-208 over a wired interface. Alternatively, the tremor sensors 204-208 can be equipped with their own power supply, which can be similar to the power supply of the NSSD 105 or controlling device 202 as described above.

The controlling device 202 can poll the tremor sensors 204-208 for tremor data. Alternatively, the tremor sensors 204-208 can signal the controlling device 202 when tremors are detected. The controlling device 202 can process the tremor sensing data singly or in combination with the sensing data supplied by the NSSD 105 to detect a neurological malfunction according to any of the algorithms described above. Once a determination is made that a neurological malfunction is probable or has occurred, the controlling device 202 can identify an electrical sequence to be applied by the NSSD 105 to mitigate the probable or actual neurological malfunction. With a sufficiently large non-volatile memory, the controlling device 202 can store a historical trace of sensing data from the NSSD 105 and tremor sensors 204-208 and subsequent electrical stimulations to mitigate neurological malfunctions. The historical trace can be used by the controlling device 202 to assist in its determination of an appropriate mitigation plan to be applied by the NSSD 105.

Figure 4:
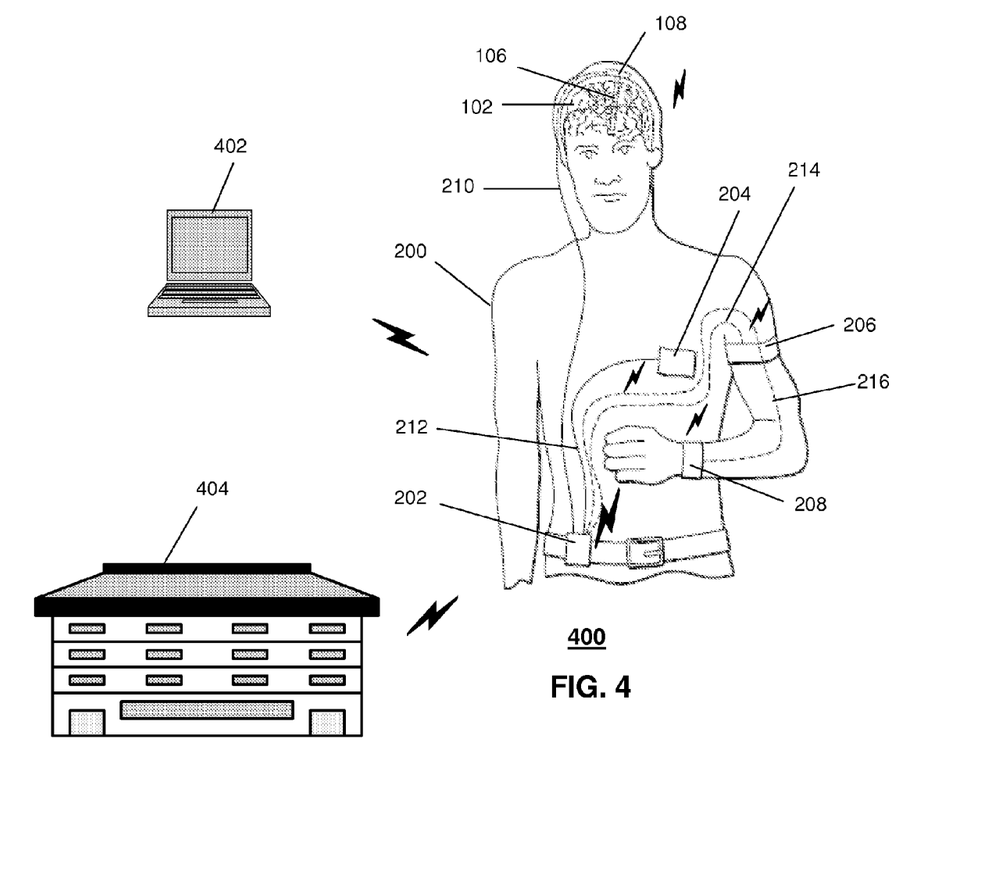
FIG. 4 depicts an illustrative embodiment of the controlling device interacting with a computing device and a medical facility.

As depicted in FIG. 4, the controlling device 202 can also utilize wireless technology to convey medically relevant information to a local computing device 402 such as a laptop or desktop computer (or PDA), and/or a medical facility 404. The transceiver 322 can utilize short-range wireless access technology such as WiFi to communicate with the computing device 402, and/or long-range wireless access technology of a cellular network operating according to a common protocol such as CDMA or GSM. The controlling device 202 can thus be an integral part of a cellular telephone tailored for medical applications and voice and data communications.

In another embodiment, the NSSD 105 and the controlling device 202 can be integrated into a single device. In this embodiment, the combined NSSD 105 and controlling device 202 can operate as closed loop system, which can be referred to as a Closed Loop Neural Device (CLND) 330. The CLND 330 can be housed in the base unit 108 shown in FIGS. 1-2. Since the NSSD 105 and the controlling device 202 are housed together, one of the power supplies 310 or 322 can be eliminated. The CLND 330 can be coupled to the tremor sensors 204-208 by a wired or wireless interface as shown in FIG. 2. In this embodiment, the housing assembly of the controlling device 202 shown on the patient's belt in FIG. 2 can be eliminated.

The CLND 330 can sense neurological sensing data by way of the neural sensor 302 coupled to the sensor leads 109 and/or the tremor sensors 204-208. Said data can be processed by the controller 320 to detect a neurological malfunction. Once a malfunction is detected an electrical stimulus can be identified by the controller 320, which can be applied by the stimulator 304 as directed by the controller 320 to a portion of the brain 102 by way of the stimulator leads 107 to mitigate the malfunction. The CLND 330 provides the patient the convenience of less devices to be carried thereby.

Figure 5:
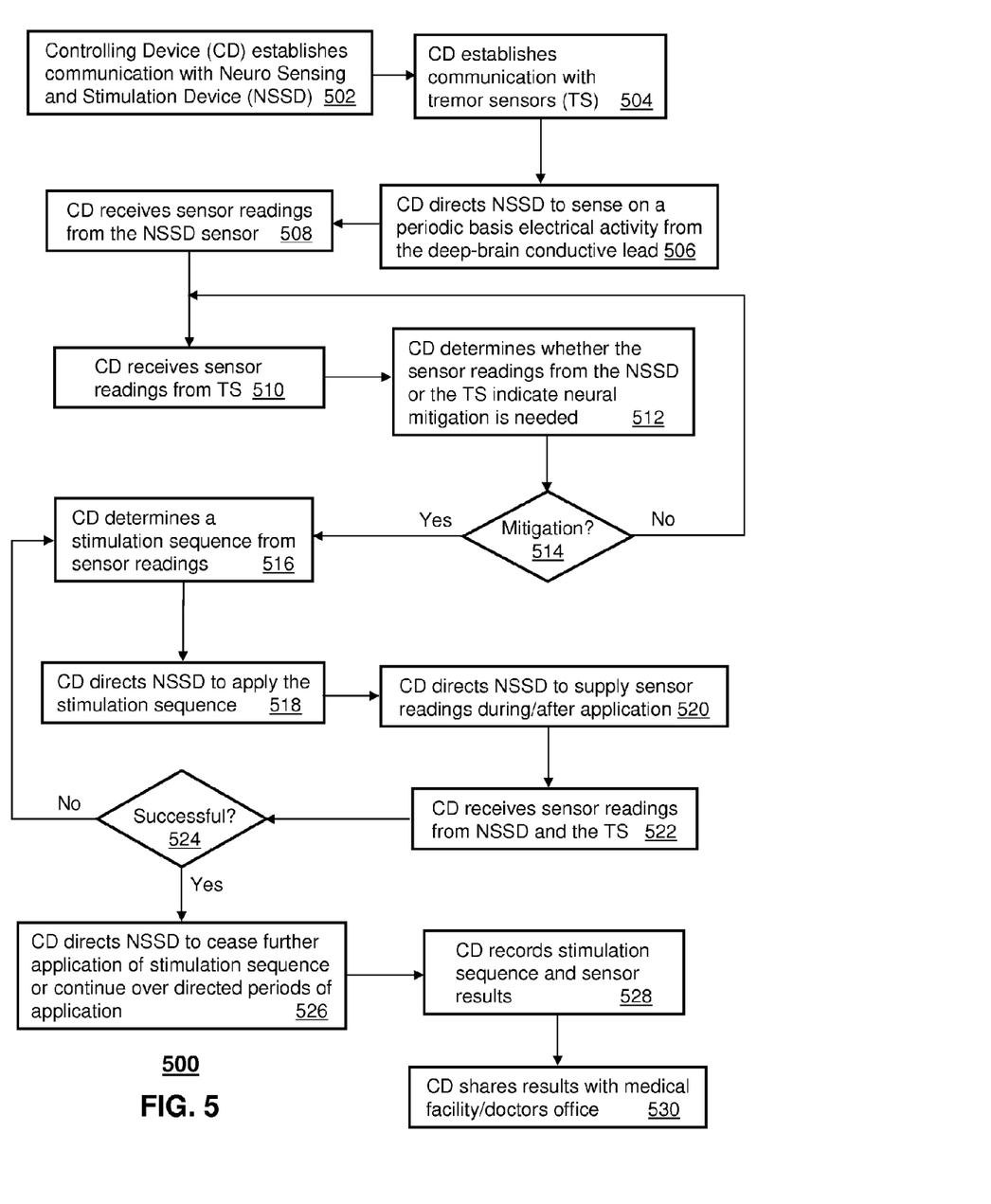
FIG. 5 depicts an illustrative embodiment of a method operating in the illustrative embodiment of FIG. 4.

FIG. 5 depicts an illustrative embodiment of a method 500 operating in the illustrative embodiments of FIGS. 3-4. For illustration purposes only, method 500 assumes that the NSSD 105 and the controlling device 202 are housed in separate assemblies as shown in FIGS. 2 and 4. It will be appreciated however that method 500 can be easily adapted to describe the operations of the CLND 330. With this in mind, method 500 can begin with step 502 in which the controlling device 202 establishes communications with the NSSD 105 by a wired or wireless interface as previously described. In step 504, the controlling device 202 can also establish communications with at least one of the tremor sensors 204-208 by a wired or wireless interface as described above. In step 506, the controlling device 202 can direct the NSSD 105 to sense on a periodic basis neurological signals through the sensing leads 109. The controlling device 202 can receive neurological signals from the NSSD 105 in step 508, and tremor sensing data in step 510 from the tremor sensors 204-208.

In step 512, the controlling device 202 can determine by way of signal processing whether the sensing data from the NSSD 105 and/or the tremor sensors 204-208 indicate a neurological malfunction thereby warranting mitigation. Step 512 can be performed with any of the signal processing algorithms previously discussed (e.g., wavelet transform, neural network, etc.). If in step 514, the controlling device 202 detects that mitigation is necessary, the controlling device 202 can proceed to step 516 where it determines by way of signal processing of the sensor readings of the NSSD 105 and/or tremor sensors 204-208 a stimulation sequence that is most likely to reduce or eliminate the malfunction. The stimulation sequence can represent in certain realizations, a stochastic random sequence having certain variances and durations determined in step 516 which can be provided from a random signal generator incorporated in the stimulation generator 304. Once a stimulation sequence is determined, the controlling device 202 can proceed to step 518 where it directs the NSSD 105 to apply the stimulation sequence determined in step 516 by way of stimulation generator 304 supplying electrical signals to the stimulator leads 107.

In step 520, the controlling device 202 can also direct the NSSD 105 to supply sensing data from the electrodes 109 of the conductive lead 106 during or after the stimulation sequence has been applied. Upon receiving the sensing data from the NSSD 105 and/or the tremor sensors 204-208, the controlling device 202 can determine in step 524 whether the neurological malfunction has been successfully reduced to a desirable level or eliminated altogether. If the mitigation is not successful, the controlling device 202 can proceed to step 516 where it can determine a new stimulation sequence according to the latest readings in step 522. If on the other hand mitigation was successful, the controlling device 202 can proceed to step 526 where it can direct the NSSD 105 to cease further application of the stimulation sequence or continue the stimulation over periodic cycles. For example, the controlling device 202 can direct the NSSD 105 to apply the stimulation sequence determined in step 516 every 6 milliseconds (or 167 stimulation cycles per second) and monitor brain activity between stimulation cycles.

The controlling device 202 can record in step 528 the stimulation sequences determined in step 516 with the sensing data supplied by the NSSD 105 and/or the tremor sensors 204-208 used to determine the stimulation sequence. The controlling device 202 can share in step 530 the recorded data in real-time or over periodic intervals (e.g., once every 24 hours) with a medical facility or a doctor's office as shown in FIG. 4. The controlling device 202 can transmit this information to the medical facility or doctor's office by way of a cellular network, or an Internet Service Provider (ISP) network connected to the controlling device 202 over a wired or wireless interface.

Method 500 can be used to mitigate any number of neurological malfunctions such as Parkinson's disease, Epilepsy, and other neurological disorders.

Upon reviewing the aforementioned embodiments, it would be evident to an artisan with ordinary skill in the art that said embodiments can be modified, reduced, or enhanced without departing from the scope and spirit of the claims described below. For example, the NSSD 105 can be directed by the controlling device 202 to apply combinations of stimulation sequences at the same time or at alternating cycles (e.g., stimulation sequence 1 followed by stimulation sequence 2, . . . ). In yet another embodiment, the NSSD 105 can be equipped with more than one conductive lead 106 for implanting in several sections of the patient's brain. In this embodiment, the NSSD 105 can be directed to sense and stimulate different portions of the patient's brain. In another embodiment, more than one NSSD 105 can be implanted in the patient 100, with each NSSD 105 controlled by the controlling device 202.

Although not shown, the NSSD 105 can use a housing assembly that allows for serviceability and replacement of components. For instance, the base unit 108 can be constructed so that it can be readily disconnected from the conductive lead 106 and replaced with another base unit 108 or the same after it has been serviced. Alternatively, or in combination the base unit 108 can have a compartment that can be opened to replace one or more rechargeable batteries on a periodic basis.

It should also be noted that a living entity in the present disclosure can also mean non-human living entities with a neurological system (e.g., a horse, a dog, a cat, etc.).

The foregoing embodiments illustrate to an artisan of ordinary skill in the art that other suitable modifications can be applied to the present disclosure. Accordingly, the reader is directed to the claims for a fuller understanding of the breadth and scope of the present disclosure.

Figure 6:
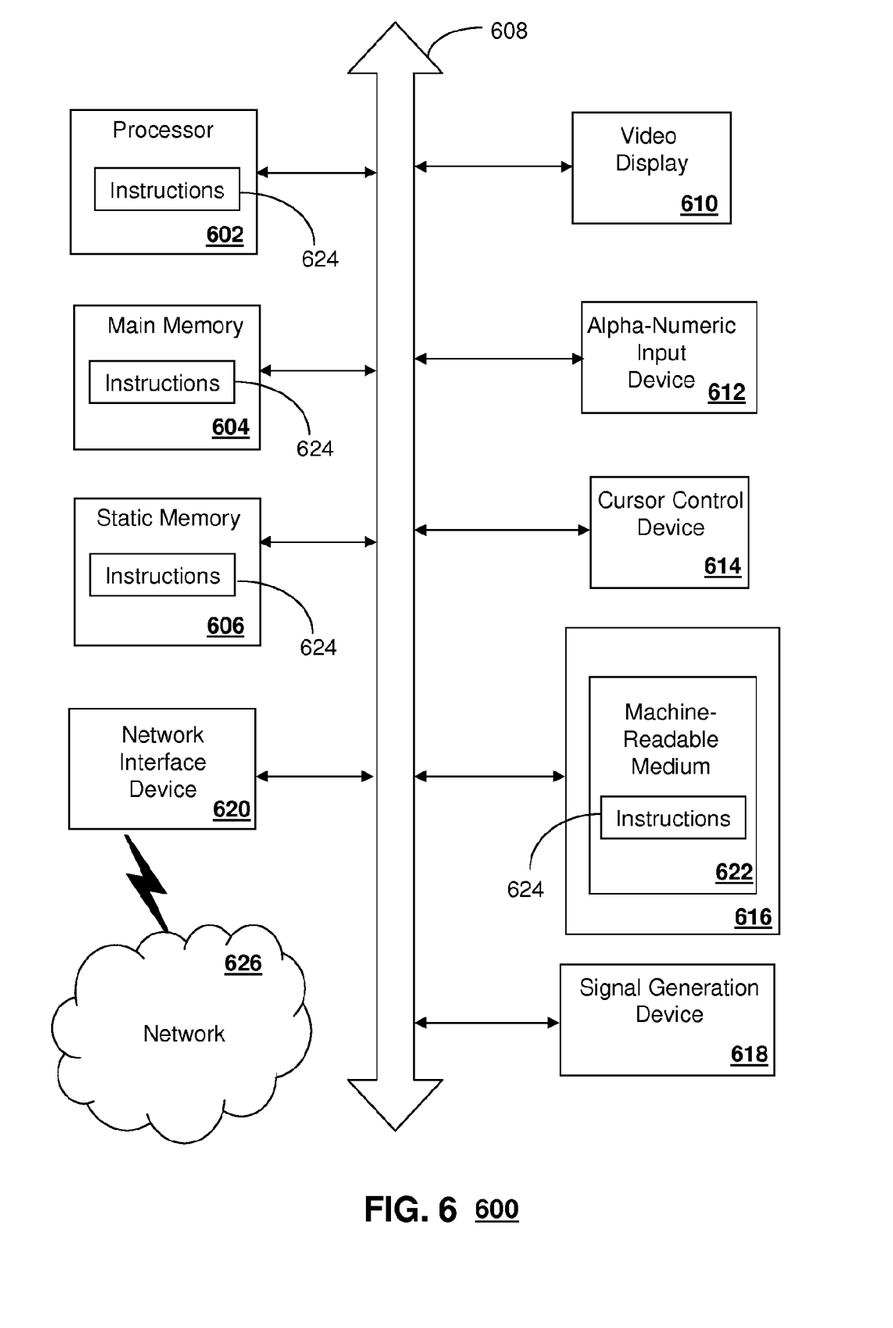
FIG. 6 depicts an illustrative diagrammatic representation of a machine in the form of a computer system within which a set of instructions, when executed, may cause the machine to perform any one or more of the methodologies disclosed herein.

FIG. 6 depicts an exemplary diagrammatic representation of a machine in the form of a computer system 600 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 600 may include a processor 602 (e.g., a central processing unit (CPU), a graphics processing unit (GPU, or both), a main memory 604 and a static memory 606, which communicate with each other via a bus 608. The computer system 600 may further include a video display unit 610 (e.g., a liquid crystal display (LCD), a flat panel, a solid state display, or a cathode ray tube (CRT)). The computer system 600 may include an input device 612 (e.g., a keyboard), a cursor control device 614 (e.g., a mouse), a disk drive unit 616, a signal generation device 618 (e.g., a speaker or remote control) and a network interface device 620.

The disk drive unit 616 may include a machine-readable medium 622 on which is stored one or more sets of instructions (e.g., software 624) embodying any one or more of the methodologies or functions described herein, including those methods illustrated above. The instructions 624 may also reside, completely or at least partially, within the main memory 604, the static memory 606, and/or within the processor 602 during execution thereof by the computer system 600. The main memory 604 and the processor 602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 624, or that which receives and executes instructions 624 from a propagated signal so that a device connected to a network environment 626 can send or receive voice, video or data, and to communicate over the network 626 using the instructions 624. The instructions 624 may further be transmitted or received over a network 626 via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A Neuro Sensing and Stimulation Device (NSSD), comprising:
   a conductive lead for implanting in a brain of a living entity, the conductive lead having a first portion for stimulation and a second portion for sensing;
   a sensor coupled to the second portion of the conductive lead for collecting data in the brain associated with one or more electrical signals detected in the conductive lead;
   a stimulator coupled to the first portion of the conductive lead to apply one or more electrical signals thereto;
   a controller operable to:
   collect data associated with one or more electrical signals detected in the conductive lead;
   process the collected data to determine a stimulation sequence from the collected data; and
   direct the stimulator to apply on the conductive lead one or more electrical signals determined from the stimulation sequence, wherein the controller communicates wirelessly with at least one of the sensor and the stimulator, and wherein the controller is operable to employ an artificial neural network (ANN) analysis on the collected data to determine a diagnosis.

2. The NSSD of claim 1, wherein the one or more electrical signals applied to the conductive lead reduce the effects of a malfunction in the brain of the living entity, and wherein the wireless coupling between the controller and at least one of the sensor and the stimulator operates according to one of a Bluetooth, WiFi, and cellular access technology.

3. The NSSD of claim 2, wherein the living entity is a human being, wherein the malfunction is associated with Parkinson's disease, and wherein the sensor and the stimulator are housed in a first housing assembly coupled to the conductive lead, wherein the controller is housed in a second housing assembly, wherein the first and second housing assemblies are coupled to each other over one of a wired interface and a wireless interface, and wherein the first housing assembly is positioned at or near the head of the human being, and wherein the second housing assembly is positioned away from the head of the human being.

4. The NSSD of claim 1, wherein the collected data is processed by the controller to detect a malfunction in the brain of the living entity, and wherein a portion of the NSSD is replaceable.

5. The NSSD as in claim 1, comprising a battery-operated power supply to power at least a portion of the NSSD, and wherein the battery-operated power supply is powered by at least one of wireless signals, body heat, kinetic motion, inductive coupling, and light.

6. The NSSD of claim 1, comprising a tremor sensor coupled to the living entity and to the controller for determining whether to apply the one or more electrical signals to the conductive lead.

7. The NSSD of claim 6, wherein the controller is operable to:
   receive tremor sensor data from the tremor sensor when a tremor is detected;
   determine the stimulation sequence according to the tremor sensor data.

8. The NSSD of claim 6, wherein the tremor sensor corresponds to an electromyographic (EMG) sensor comprising one or more EMG electrodes.

9. The NSSD of claim 8, wherein the EMG electrodes are placed on a surface of the living entity.

10. The NSSD of claim 1, wherein the controller is operable to:
    detect from the collected data a malfunction in the living entity; and
    determine from the malfunction the stimulation sequence.

11. The NSSD of claim 10, wherein the controller is operable to utilize at least one of a wavelet transform, a neural network, and a least squares identification to detect and to analyze the malfunction in the living entity in order to determine the stimulation sequence.

12. The NSSD of claim 1, wherein the controller is operable to utilize prior historical data collected from the NSSD in the ANN analysis.

13. The NSSD of claim 1, wherein the ANN is a LAMSTAR ANN.

14. A Controlling Device (CD), comprising a controller to:
    direct a Neuro Sensing and Stimulation Device (NSSD) having a conductive lead implanted in a brain of a living entity to supply sensing data derived from electrical activity sensed from the brain and for stimulating the brain, the conductive lead having a first portion for stimulation and a second portion for sensing;
    receive from the NSSD sensing data collected by the NSSD by way of the second portion of the conductive lead;
    process the collected sensing data to determine stimulation instructions from the collected sensing data; and
    direct the first portion of the NSSD to apply one or more electrical signals to the brain of the living entity according to the stimulation instructions, wherein the controller is operable to employ an artificial neural network (ANN) analysis on the collected sensing data to determine a diagnosis.

15. The CD of claim 14, wherein the living entity comprises one of a human being or an animal, wherein the CD comprises a battery-operated power supply to power the controller, and wherein the battery-operated power supply is powered by at least one of wireless signals, body heat, kinetic motion, inductive coupling, and light.

16. The CD of claim 14, wherein the one or more electrical signals applied by the NSSD reduces the effects of a malfunction in the brain of the living entity.

17. The CD of claim 16, wherein the living entity is a human being, and wherein the malfunction is associated with Parkinson's disease.

18. The CD of claim 14, wherein the controller is operable to process the collected data to detect a malfunction in the brain of the living entity.

19. The CD of claim 18, wherein the controller is operable to generate the stimulation instructions responsive to the processed collected data.

20. The CD of claim 18, wherein the controller is operable to detect the malfunction according to a pattern in the collected data that identifies an abnormality in the brain of the living entity.

21. The CD of claim 20, wherein the controller is operable to detect the pattern according to a historical trend or variance in the collected data.

22. The CD of claim 18, wherein the controller is operable to process the collected data according to one of a wavelet transform, a neural network, and a least squares identification to detect the malfunction in the brain of the living entity.

23. The CD of claim 14, wherein the stimulation instructions correspond to a stimulation profile that reduces the effects of the malfunction.

24. The CD of claim 23, wherein the controller is operable to adapt the stimulation profile according to a historical trend.

25. The CD of claim 14, wherein the controller is operable to transmit wireless signals directed to a medical facility, wherein the wireless signals include the collected data received from the NSSD, and wherein the medical facility analyzes the collected data.

26. The CD of claim 25, wherein the controller is operable to receive wireless signals from the medical facility providing instructions for managing the NSSD according to the analyzed collected data.

27. The CD of claim 26, wherein the wireless signals exchanged between the CD and the medical facility operate according to a cellular wireless access technology corresponding to one of GSM, CDMA, UMTS, and WiMAX access technologies.

28. The CD of claim 27, wherein the CD is housed in an accessory that is electromechanically coupled to the cellular telephone that conveys messages between the medical facility and the CD.

29. The CD of claim 27, wherein the CD is housed in an accessory that is wirelessly coupled to a cellular telephone that conveys messages between the medical facility and the CD, wherein the wireless coupling between the CD and the cellular telephone operates according to a Bluetooth or WiFi access technology.

30. The CD of claim 27, wherein the CD is an integral part of a cellular telephone that conveys messages between the medical facility and the CD.

31. The CD of claim 14, wherein the controller is operable to utilize prior historical sensing data collected from the NSSD in the ANN analysis.

32. The CD of claim 14, wherein the ANN is a LAMSTAR ANN.

33. The CD of claim 14, wherein the stimulation instructions comprise stimulus parameters comprising at least one of a timing profile, an amplitude profile, a frequency profile, a pulse-width profile, and a pulse-shape profile for applying the one or more electrical signals.

34. The CD of claim 14, wherein the CD wirelessly communicates with the NSSD utilizing a wireless access protocol corresponding to at least one of a secure communication channel between the CD and the NSSD, a noise suppression filter to suppress noise in the communication channel, and a self-adaptive noise filter to adapt to noise in the communication channel.

35. The CD of claim 14, further comprising a stimulation generator coupled to the conductive lead for applying signals to a portion of the brain, a neural sensor coupled to the conductive lead for sensing electrical activity in the portion of the brain, and a power supply to supply energy to the stimulation generator, the sensor, and the controller, and wherein the stimulation generator applies signals to the portion of the brain according to a stochastic sequence generated by a random signal generator, wherein the power supply is battery operated, and wherein the battery-operated power supply comprises a trickle charger which charges one or more batteries by extracting energy from at least one of wireless signals, body heat, kinetic motion, inductive coupling, and light.

* * * * *